(12) United States Patent
Nürnberger et al.

(10) Patent No.: US 12,251,505 B2
(45) Date of Patent: Mar. 18, 2025

(54) DIALYSIS DEVICE FOR PERFORMING A DIALYSIS TREATMENT

(71) Applicant: Fresenius Medical Care Deutschland GmbH, Bad Homburg (DE)

(72) Inventors: Thomas Nürnberger, Burkardroth (DE); Stefan Kellermann, Massbach (DE)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 1200 days.

(21) Appl. No.: 17/044,921

(22) PCT Filed: Apr. 4, 2019

(86) PCT No.: PCT/EP2019/058494
§ 371 (c)(1),
(2) Date: Oct. 2, 2020

(87) PCT Pub. No.: WO2019/193090
PCT Pub. Date: Oct. 10, 2019

(65) Prior Publication Data
US 2021/0154386 A1    May 27, 2021

(30) Foreign Application Priority Data
Apr. 4, 2018 (DE) .............. 10 2018 107 967.2

(51) Int. Cl.
*A61M 1/36* (2006.01)
*A61M 1/16* (2006.01)

(52) U.S. Cl.
CPC ........ *A61M 1/3639* (2013.01); *A61M 1/1601* (2014.02); *A61M 1/3656* (2014.02);
(Continued)

(58) Field of Classification Search
CPC .............. A61M 1/3639; A61M 1/1601; A61M 1/3656; A61M 2205/15; A61M 2205/3331; A61M 2205/702
See application file for complete search history.

(56) References Cited

U.S. PATENT DOCUMENTS

| 6,601,432 | B1 | 8/2003 | Ericson et al. |
| 9,452,252 | B2 | 9/2016 | Kopperschmidt |

(Continued)

FOREIGN PATENT DOCUMENTS

| DE | 3720667 | 1/1989 |
| DE | 102008015832 | 10/2009 |

(Continued)

OTHER PUBLICATIONS

PCT International Preliminary Report on Patentability in International Appln. No. PCT/EP2019/058494, mailed Oct. 15, 2020, 16 pages (with English translation).
(Continued)

*Primary Examiner* — Benjamin L Lebron
(74) *Attorney, Agent, or Firm* — Fish & Richardson P.C.

(57) ABSTRACT

A dialysis device for performing a dialysis treatment can include a liquid conducting system, which comprises a first section and a second section. A differential pressure sensor can be included for measuring a differential pressure $p_{diffm}$ between a first pressure ($p_1$) in the first section of the liquid conducting system and a second pressure ($p_2$) in the second section of the liquid conducting system. A monitoring unit is also provided, which is configured to determine an operating status based on the measured differential pressure $p_{diffm}$. A control device is also provided, which is configured to interrupt and/or block the dialysis treatment according to the determined operating status. A display device is also pro-
(Continued)

vided, which is configured to output a notification based on the determined operating status.

10 Claims, 9 Drawing Sheets

(52) U.S. Cl.
CPC . *A61M 2205/15* (2013.01); *A61M 2205/3331* (2013.01); *A61M 2205/702* (2013.01)

(56) References Cited

U.S. PATENT DOCUMENTS

| | | |
|---|---|---|
| 9,925,323 B2 | 3/2018 | Ekdahl et al. |
| 2011/0034814 A1 | 2/2011 | Kopperschmidt |
| 2012/0318740 A1 | 12/2012 | Ekdahl et al. |
| 2016/0325034 A1 | 11/2016 | Wiktor et al. |

FOREIGN PATENT DOCUMENTS

| | | |
|---|---|---|
| DE | 102014000678 | 7/2015 |
| JP | 2002-535611 | 10/2002 |
| JP | 2011-515166 | 5/2011 |
| WO | WO 00/42406 | 7/2000 |
| WO | WO 2009/118145 | 10/2009 |

OTHER PUBLICATIONS

PCT International Search Report and Written Opinion in International Appln. No. PCT/EP2019/058494, dated Jun. 27, 2019, 19 pages (with English translation).

DIALYSIS DEVICE FOR PERFORMING A DIALYSIS TREATMENT

CROSS-REFERENCE TO RELATED APPLICATIONS

The present application is the national stage entry of International Patent Application No. PCT/EP2019/058494, filed on Apr. 4, 2019, and claims priority to Application No. DE 10 2018 107 967.2, filed in the Federal Republic of Germany on Apr. 4, 2018, the disclosures of which are expressly incorporated herein in entirety by reference thereto.

FIELD OF THE INVENTION

The present disclosure pertains to a dialysis device for performing a dialysis treatment and a method for monitoring an operating status of a dialysis device.

BACKGROUND

Various methods for blood treatment of a patient, in particular for purifying and draining or de-watering the blood of a patient are known.

For example, in hemodialysis the blood of a patient is purified in an extracorporeal blood circuit, which comprises a dialysis filter. The dialysis filter comprises a blood space, through which the blood of the patient is conducted, and a dialysate space. The blood space and the dialysate space are separated from each other by a semipermeable membrane, for example in the form of hollow fibers, wherein the walls of said fibers form the membrane. During hemodialysis the dialysate space is perfused with dialysate and the blood space is perfused with the blood of the patient. Due to a concentration gradient between the dialysate and the blood of the patient substances are transported through the semipermeable membrane by diffusion.

Further methods for blood purification are known, such as e.g. hemofiltration, wherein the transport of substances through the semipermeable membrane is provided by a pressure gradient. Hemodiafiltration combines the hemodialysis and the hemofiltration.

The extracorporeal blood circuit essentially comprises an arterial tubing system, through which the blood of the patient that is to be purified is fed to the dialyzer, and a venous tubing system, through which the purified blood is returned from the dialyzer back to the patient. The tubing system may include a cassette, wherein the tubing is at least partially formed by e.g. rigid liquid flow paths or channels in the cassette.

Both tubing systems may each be connected to one or more pressure sensor(s) of the dialysis device, which determine the pressure before and after the dialysis filter, or determine the pressure in the arterial tubing system and in the venous tubing system. This may serve the purpose that a reliable and safe dialysis is ensured. To ensure reliable pressure monitoring the functioning of the safety relevant pressure sensors can be regularly verified or checked. Accordingly, the system is required to be monitored prior to and/or during the treatment with respect to its functionality, or during the treatment with respect to a failure or malfunctioning according to the standard IEC 60601-2-16.

In order to check the functioning of the pressure sensors multiple methods are known. In said methods, the pressure sensors are initially verified in a zero-point such as at atmospheric pressure. However, in order to check the functioning of the pressure sensor with a known transfer function (in the form of y=mx+t), a further measuring point is required. This may be detected at the pressure sensor by application of an additional pressure, which requires an elaborate and cumbersome pneumatic tubing system to decouple the test pressure of both pressure sensors. A further possibility exists, wherein the second measuring point is determined by means of an electronic detuning of the sensor signal. This, however, has the disadvantage that only the functioning of the signal path after the pressure sensor may be checked or examined, whereas the functioning of the sensor itself and including its sensor membrane cannot be tested.

A further possibility for monitoring the functioning of the pressure sensors exists, wherein for each pressure sensor a respective second, redundant sensor is used. However, this significantly increases the overall costs.

In addition, the possibility exists to retrieve an additional measuring point via a so-called coupling test. For example, the venous pressure is increased by closure of a clamp and the achievement of a pressure threshold (e.g. a venous scale end) is checked. However, the test can only be started when a tubing system is inserted and filled with a fluid, since no sufficient pressure change may be built when compressing air, e.g., in an unfilled or empty tubing system. Furthermore, the performance of a coupling test is very demanding with respect to the tubing system, since a tight clamping of the tubing system must be facilitated at the start of the treatment or already during the preparation of a treatment.

SUMMARY

In some embodiments, the present disclosure describes an improved dialysis device for performing a dialysis treatment as well as a method for monitoring a pressure measuring device and a method for determining an operating status.

Example embodiments are described in the present description and the Figures.

Accordingly, a dialysis device for performing a dialysis treatment, comprising a liquid conducting system, which comprises a first section and a second section, is described herein. According to some embodiments described herein, a differential pressure sensor is provided for measuring a differential pressure $p_{diffm}$ between a first pressure in the first section of the liquid conducting system and a second pressure in the second section of the liquid conducting system, wherein a monitoring unit is provided, which is configured to determine an operating status based on the measured differential pressure Nam, and wherein furthermore a control device is provided, which is configured to interrupt and/or block the dialysis treatment according to the determined operating status, and/or a display device is provided, which is configured to output a notification based on the determined operating status.

Since the differential pressure sensor is provided between the first section and the second section of the liquid conducting system, the pressure difference may be monitored in a reliable fashion and/or the pressure sensors, which are arranged on the individual sections of the liquid conducting system, may be examined or checked as to their functioning.

By measuring the differential pressure, the correct process of the dialysis treatment may be monitored and/or examined with regard to the functioning, such that the safety of the patient to be treated is increased. For example, when an undesirable deviation of the differential pressure occurs during the dialysis treatment, a notification, for example an error notification, may be outputted and/or the dialysis may be stopped and/or the beginning of a subsequent treatment may be blocked.

The liquid conducting system may comprise two or more sections from the group of an arterial patient line, a venous patient line, a pre-dialyzer dialysate line, a post-dialyzer dialysate line, a substitute line, a water input line, and a concentrate feed line. These sections may each be connected to a pressure sensor to measure the pressure in the lines, and the pressure sensor for measuring a differential pressure between the pressures in the first section and the second section may be provided between each of these sections.

A dialysis device in general facilitates the patient-specific removal of solved substances (e.g. urea, creatinine, vitamin B12 or β2-Microglobuline) as well as a defined amount of water, if required, from the blood in kidney replacement therapies. Such a dialysis device may be used both for hemodialysis and a hemofiltration or hemodiafiltration. Furthermore, the dialysis device may be an ultrafiltration device. Accordingly, water is removed from the blood without a purification of the blood. The dialysis device may furthermore be an acute dialysis device. Accordingly, the dialysate may be transferred from a bag into the dialysate circuit and may be transferred from the dialyzer into a bag.

The monitoring of the operating status may be performed by monitoring blood in the extracorporeal circuit or another liquid, in particular a dialysis liquid, a filling or priming liquid, in the liquid conducting system. If the monitoring is performed with a liquid other than blood, this may be performed before and/or after the treatment, such that it may be ensured that at least before and/or after the treatment a safely functioning dialysis device is provided.

The pressure in the first section, if said section relates to the arterial patient line in the area or range of the blood withdrawal point of the blood from an arterial patient access of a patient, is also referred to as arterial pressure, and the pressure in the second section, if said section relates to the venous patient line in the area or range of the blood feed or return point of the blood from a venous patient access of a patient, is also referred to as venous pressure. The setting and detection of both of these pressures may be required for various purposes. They may be of importance for the safety of the patient during the dialysis treatment or may be used for controlling the blood flow and/or the dialysis treatment.

In some embodiments, said differential pressure sensor is arranged between the first section and the second section.

The term differential pressure sensor is to be understood as a pressure sensor, which measures the difference between two absolute pressures, i.e. a differential pressure. The differential pressure sensor may, for example, consist of two measurement clamps, which are hermetically separated from each other by a membrane. The deflection of the membrane then relates to a measure of the size of the pressure. Using said differential pressure sensor e.g. the differential pressure $p_{diffm}$ between the pressure in the first section $p_1$ and the pressure in the second section $p_2$ is measured. Between said exemplary pressures the following relation exists:

$$p_{diffm} = p_1 - p_2 \qquad (1)$$

The monitoring unit detects the values measured by the differential pressure sensor and then determines the operating status based thereon. This may e.g. be determined by comparing the measured values with nominal values for a differential pressure for particular operating statuses or by monitoring a change of a differential pressure over time, wherein in the occurrence of a sudden change of the differential pressure an anomaly or an undesirable operating status is determined.

In case of a nominal value also a nominal course may be provided, such that a value being constant over time is not required.

Further, the operating statuses refer to various desirable or undesirable statues of the dialysis method and/or the dialysis device.

A desirable operating status refers, for example, to the case wherein the differential pressure is essentially constant, is repeated periodically, or does not indicate a drift, or wherein one or more specific components of the pressure signal do not change over time, such that the dialysis may be performed in an effective and safe manner. Said components may refer to the maximum amplitude of the pressure signal, a phase of the pressure signal, and/or a frequency component of the pressure signal, as may be derived, e.g. from the periodic pressure signal by means of Fourier transformation.

An undesirable status may e.g. be present, when the venous needle, via which the purified blood is fed or returned to the patient, is accidentally disconnected from the venous patient access of the patient (VND, Venous Needle Disconnect) and accordingly an error situation occurs. In such case, blood exits the blood return in an uncontrollable manner, which may hence not be returned to the patient, such that a dangerous blood loss may develop for the patient. Since the contact between the venous needle and the patient is disconnected, the pressure in the blood return is reduced, such that the differential pressure between the blood feed and the blood return drops (is reduced). This change in the differential pressure may be detected by the monitoring unit as an undesirable operating status.

A further undesirable operating status may be that at least one of the pressure sensors does not function correctly and that the pressure measured with said pressure sensor is not correct.

If an undesirable operating status is detected by the monitoring unit, the monitoring unit may immediately initiate the interruption of the dialysis process to avoid a safety hazard of the patient and/or output a notification, e.g., an alarm signal or an error message or notification. An intervention may also be that the control of the device is blocked before the treatment. The measure in reaction to the undesirable operating status may be taken immediately after the corresponding detection or at a later time point. For example, it may be possible, that an actual treatment is continued and the measure is taken only after said treatment.

Since various operating statuses of a dialysis device may be determined by the monitoring unit based on a measured differential pressure between the first section and the second section, a simple and reliable solution for the monitoring of the correct functioning of a dialysis device is provided. Undesirable operating statues may be determined in a fast and reliable way and it may be accordingly intervened in the operating process of the dialysis device, directly or at a predefined time point or event, to avoid a safety hazard for the patient, for example due to an increased loss of blood.

A first pressure sensor for measuring a pressure in the first section and a second pressure sensor for measuring a pressure in the second section may be provided, and the monitoring unit may be configured to calculate a differential pressure $p_{diffb}$ of the first measured pressure in the first section versus the second measured pressure in the second section.

According to an embodiment, a first pressure sensor for determining a pressure in a blood feed line and/or a second pressure sensor for determining a pressure in the blood return line are provided. The first and/or second pressure sensor may be provided in addition to the differential pressure sensor. Accordingly, also the actual pressure in the blood feed line and the actual pressure in the blood return line may be determined independently of the differential pressure and aside from the differential pressure between the pressure in the blood feed line, i.e. the pressure in proximity to the withdrawal point of the blood to be dialyzed, and the pressure in the blood return line, i.e. the pressure in proximity to the return point of the dialyzed blood in a patient.

The monitoring unit may determine an incorrect functioning of the first and/or second pressure sensor as an operating status.

The monitoring unit may also be configured to determine the operating status based on the calculated differential pressure $p_{diffb}$ and the measured differential pressure $p_{diffm}$. In order to determine the operating status, the monitoring unit may be configured to determine a difference $p_{res}$ between the calculated differential pressure $p_{diffb}$ and the measured differential pressure $p_{diffm}$ and to compare the determined difference $P_{res}$ with a nominal value.

According to a further embodiment, the monitoring unit is configured to determine a correct functioning of the first and/or the second pressure sensor based on the measured differential pressure and a differential pressure calculated from the pressure measured in the first section and in the second section, preferably taking into account a differential pressure $p_{diffb}$ calculated from the measured pressure in the first section and the measured pressure in the second section. For example, the first pressure sensor may be a pressure sensor arranged at the arterial patient line for measuring the pressure and the second pressure sensor may be a pressure sensor arranged at the venous patient line for measuring the pressure.

To monitor the correct functioning of the pressure sensors, the absolute pressure in the first section may be measured by the first pressure sensor and the absolute pressure in the second section may be measured by the second pressure sensor independently of the differential pressure. From the measured pressure in the first section and the measured pressure in the second section a differential pressure $p_{diffb}$ may be determined or calculated. The monitoring unit may then be configured to compare the measured differential pressure $p_{diffm}$ between the pressure in the first section and the pressure in the second section with the determined/calculated differential pressure $p_{diffb}$. When both differential pressure values are subtracted from each other, a resulting pressure $p_{res}$ is obtained. When the first and second pressure sensor measure correctly and the differential pressure sensor measures correctly, the values of the measured and the calculated differential pressure are equal, such that a resulting pressure of zero is obtained. Between said pressures, again provided exemplary for the pressures $p_1$ and $p_2$, the following relation exists:

$$p_{res}=(p_1-p_2)-p_{diffm} \quad (2)$$

Since the measurement of the pressures is generally subject to tolerances to a certain extent, $p_{res}$ may also comprise a value unequal to zero, however, then comprises a constant or essentially constant value, which is obtained from the measurement tolerances of the pressure sensors.

Since a differential pressure sensor is provided in addition to a first and/or second pressure sensor, the functioning of the first and/or second pressure sensors may be checked or verified in a simple manner. Thereby, the reliability of the dialysis device and hence the safety of the patient is increased. Accordingly, also a complete functional inspection of the pressure measurement, i.e. resistance bridge, signal modification, ADC conversion, and the inputting of measurement signals may not be required. Furthermore, also a detuning of the pressure sensors may not be required to detect an offset or rate or slope error of the pressure sensors, such that an influencing of the measurement signals by the detuning path is excluded.

A further advantage may be provided by the fact that cost-efficient and standard pressure sensors may be used and no special intrinsically safe pressure sensors are required due to the redundant monitoring.

According to a further embodiment, the liquid conducting system is an extracorporeal blood circuit with a dialysis filter, wherein the first section corresponds to a blood feed line and the second section corresponds to a blood return line. In the extracorporeal blood circuit of the dialysis device the blood of the patient that is to be purified is conducted or passed through the various elements of the dialysis device outside of the body of the patient. The extracorporeal blood circuit comprises a blood feed (arterial patient line) and a blood return (venous patient line).

The blood feed line may be connected to an artery of the patient to be treated, i.e. blood to be purified from a patient is introduced into the extracorporeal circuit via the blood feed line. The propulsion of the blood to be purified may be provided by a pump. The blood return line is connected to a vein of the patient to be treated, i.e. purified blood from the extracorporeal blood circuit is provided to the body of the patient via the blood return line. Generally, the blood withdrawal and the blood return occur from or in a blood vessel that is specifically formed (shunt) or a large blood comprising vessel of the patient. A dialysis filter is provided between the feed line and the blood return of the extracorporeal blood circuit. The blood to be purified is conducted through said dialysis filter, wherein e.g. in case of hemodialysis, dialysate flows in a counter flow direction with respect to the blood to be purified and wherein the dialysate stream and the blood stream are separated from each other by a semipermeable membrane. Accordingly, undesired substances are removed from the blood and the blood is enriched with desired substances in the dialysis filter due to diffusion.

According to a further embodiment, the monitoring unit is configured to detect needle disconnect (VND, Venous Needle Disconnect) by means of the measured differential pressure $p_{diffm}$. The term needle disconnect also comprises the case, wherein a connection in the liquid conducting system is lost or disconnected, for example, a Luer connection from the tubing system to the needle or also the connection between a tubing system and dialyzer.

The detection of a needle disconnect may occur even more reliably when fewer structural parts are provided, which may influence the pressure. This may particularly be achieved when the dialysis device for performing a dialysis treatment only comprises a blood pump, a dialyzer, a venous space with a clotting filter, and a tubing system, which connects said elements, in the extracorporeal blood circuit. Hence, no elements are provided, which may particularly influence the partial pressure or generate pressure fluctuations. In particular, this device only comprises one or more pumps for the dialysate flow and a pump for the blood flow, however, no pump for transferring the dialysate or substitute liquid directly, i.e. not via the membrane of the dialyzer, into the blood tubing system.

By using the differential pressure sensors, and hence only one pressure transducer device, no errors as to linearity and no phase differences are obtained compared to the determining of the needle disconnect based on $p_{diffb}$, for which the signal of two pressure sensors are used.

A method for monitoring at least one operating status of a dialysis device comprising a liquid conducting system with a first section and a second section is described herein. The method comprises the steps of:

measuring a differential pressure $p_{diffm}$ between a first pressure in the first section and a second pressure in the second section by means of a differential pressure sensor, determining an operating status based on the measured differential pressure Nam, and interrupting a dialysis treatment and/or blocking a dialysis treatment and/or outputting a notification based on the determined operating status.

When determining a deviation of the measured differential pressure $p_{diffm}$ from a nominal value and/or when determining a predefined change of the differential pressure $p_{diffm}$ during the dialysis treatment, an undesirable operating status may be inferred.

The deviation may also be provided as a deviation from a mathematically processed measured differential pressure $p_{diffm}$. The mathematical processing may e.g. comprise a temporal averaging and/or a Fourier analysis for a frequency output evaluation and/or a subtraction of a nominal signal course.

After or upon determining an undesirable operating status a dialysis treatment is interrupted and/or blocked and/or a notification is outputted, e.g. an error notification, based on the determined operating status. If the measured/determined differential pressure Nam suddenly changes, for example, due to an accidentally disconnected venous needle or a defect liquid feed/discharge, said pressure change is detected by the monitoring unit for determining the operating status, which may then initiate an immediate interruption of the dialysis treatment to e.g. avoid a hazardous blood loss of the patient.

According to a preferred embodiment, the method comprises the steps of:

measuring a pressure in the first section by means of a first pressure sensor, measuring a pressure in the second section by means of a second pressure sensor, calculating a differential pressure $p_{diffb}$ between the measured pressure in the first section and the measured pressure in the second section Between the measured pressure in the first section, the measured pressure in the second section, and the calculated differential pressure $p_{diffb}$, the following relation is given, as exemplary described in view of the pressures $p_1$ and $p_2$:

$$p_{diffb} = p_1 - p_2 \quad (3)$$

According to an embodiment of the method, the operating status comprises an incorrect functioning of the first and/or second pressure sensor. Thereby, not only the pressure in the first and/or second section may be monitored, but additionally the correct functioning of the first and the second pressure sensor. Accordingly, it is avoided that the pressure in the first section and/or the pressure in the second section are measured incorrectly. Thereby, the safety of the dialysis method as a whole is increased.

Namely, if a pressure in the feed is incorrectly determined or a measurement error is not detected, this potentially results in an erroneous calculation of the dialyzed blood volume. If the pressure in the blood return is incorrectly determined or a measurement error is not detected, a pressure drop, which is caused by an accidentally disconnected connection to a venous needle or by a disconnection of the needle from the patient, may potentially not be detected. This can result in a blood loss and hence a severe safety hazard for the patient.

According to one embodiment of the method, it may be provided that after determining of an incorrect functioning of a first pressure sensor in a first section a pressure is determined in the first section from the measured differential pressure $p_{diffm}$ and the measured pressure in a second section.

According to a further preferred embodiment of the method, it may be provided that after determining of an incorrect functioning of a second pressure sensor in a second section a pressure is determined in the second section from the measured differential pressure Nam and the measured pressure in a first section. When a comparison between the measured and the calculated differential pressure provides that one of both pressure sensors is defective, i.e. does not measure at all or has delivered an erroneous measurement result, the missing measurement value may be calculation according to the following relations, which are again exemplary described in view of the pressures $p_1$ and $p_2$:

$$p_1 = p_2 - p_{diffm} \quad (6)$$

$$p_2 = p_1 + p_{diffm} \quad (7)$$

Since the missing measurement value may be calculated by the measured differential pressure, it is possible that even in the case of a down-time or defect or an erroneous measurement of the first and/or second pressure sensor the dialysis process may be reliably continued.

According to an embodiment, the determining of the operating status comprises a determining based on the calculated differential pressure $p_{diffb}$ and the measured differential pressure $p_{diffm}$.

The determining may comprise the following steps:

calculating a resulting pressure $P_{res}$ from the difference between the calculated differential pressure $p_{diffb}$ and the measured differential pressure $p_{diffm}$, and analyzing the behavior of the pressure $p_{res}$.

The analysis may be a comparison with a nominal value and/or an analysis of the change over time.

The resulting pressure pies is calculated as follows:

$$p_{res} = p_{diffm} - p_{diffb} \quad (4)$$

Here, a certain deviation of the resulting pressure $\Delta p_{res}$ is allowed for a monitoring, since each of the pressure sensors comprise tolerances with regard to the temperature drift, the rate or slope, or the offset. The allowable deviation may be stored in a storage or memory of the dialysis device and a processor of the dialysis device may determine by comparison whether the allowable deviation is met and/or is exceeded. Thereby, for example, an interruption of the treatment may be achieved.

The problem detected by a monitoring unit may be indicated at the latest upon a subsequent T1-test. Accordingly, for example, the occurred problem may be specified by means of a check list or may be confined to a corresponding pressure sensor.

Furthermore, the possibility exists, after the detection of a failure or error, to check which of both pressure sensors has failed by an intermediate or short-term closing of a venous clamp during the treatment.

According to an embodiment of the method, an error volume is accumulated from the resulting pressure $p_{res}$ when the resulting pressure deviates from the nominal value. When a predefined maximum error volume is exceeded, the notification is provided and/or the dialysis treatment is interrupted and/or the start of the treatment is blocked.

According to some embodiments, a notification is provided and/or the dialysis treatment is interrupted and/or the start of the treatment is blocked, when a continuous or persisting deviation of the resulting pressure $p_{res}$ from the nominal value exists or is present and a minimum trigger level is reached.

By the described monitoring method, it is possible to monitor the pressure in the first section, for example in the feed line, i.e. the arterial pressure, as well as the pressure in the second section, for example in the blood return line, i.e. the venous pressure, and the corresponding differential pressure. By means of the monitoring method the course of treatment may hence be monitored in a simple manner, such that a correct course or process and an effective treatment of the patient are ensured.

The liquid conducting system may be an extracorporeal blood circuit with a dialysis filter, wherein the first section corresponds to a blood feed line and the second section corresponds to a blood return line.

According to an embodiment of the method a needle disconnection may be detected as an operating status based on the measured differential pressure $p_{diffm}$.

The method may be performed by the dialysis device described in the above, that is, all features described with respect to the dialysis device are also disclosed for the method and vice versa.

BRIEF DESCRIPTION OF THE FIGURES

Example embodiments are described in further detail in the following description in connection with the accompanying drawings, in which it is shown.

DETAILED DESCRIPTION OF THE FIGURES

Figure 1:
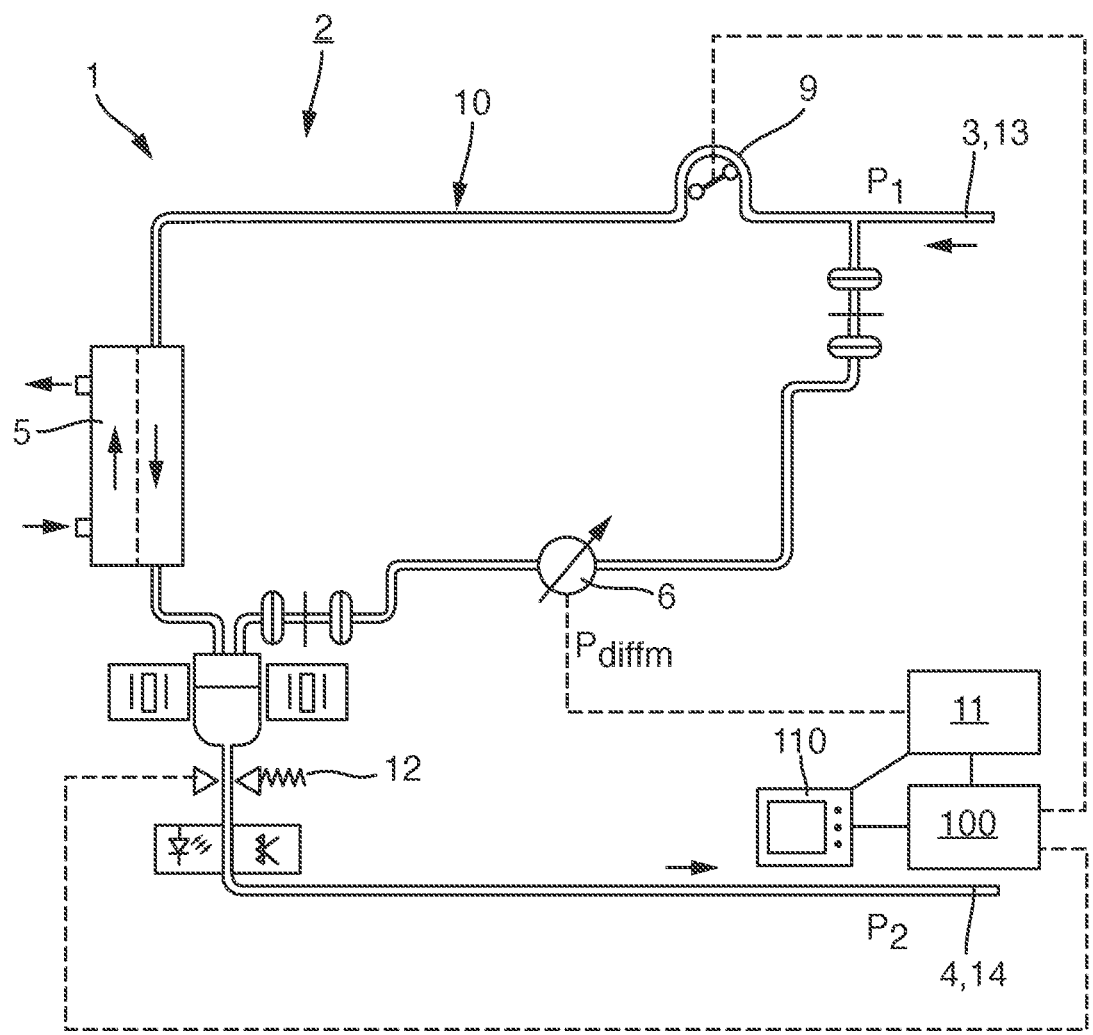
FIG. 1 shows a dialysis device with an extracorporeal blood circuit of a dialysis device with a differential pressure sensor between a blood feed and a blood return.

In the following, further example embodiments will be explained in more detail with reference to the accompanying Figures. In the various Figures, like elements are denoted by identical reference numerals and repeated description thereof may be omitted in order to avoid redundancies.

In the following description, a dialysis device 1 for performing a dialysis treatment and a method for monitoring at least one operating status of the dialysis device 1 are described. The dialysis device 1, which has already been described in general in the above, is depicted in the Figures very schematically and exemplary in regard to an extracorporeal blood circuit 10 with at least a dialysis filter 5 and a liquid conducting system 2.

Accordingly, a dialysis device 1 with a liquid conducting system 2 is schematically shown in FIG. 1, wherein the liquid conducting system 2 is an extracorporeal blood circuit 10. For the further description, a blood feed corresponds to a first section 3 of the liquid conducting system 2 and a blood return corresponds to a second section of the liquid conducting system 2.

The dialysis device 1 furthermore comprises a dialysis filter 5, which is arranged between the blood feed line 13 and the blood return line 14. The blood feed line 13, also called arterial feed line, is connected to the patient via a connection, not shown, to withdraw blood from the circuit or circulation of the patient. By the same token, the blood return line 14, also called venous return line, is also connected to the patient via a connection, not shown, to return the blood treated in the dialysis filter 5 to the circuit or circulation of the patient.

The dialysis device 1 furthermore comprises a pump 9, which is depicted in the form of a flexible tube or peristaltic pump, in order to feed the blood withdrawn from the patient through the extracorporeal blood circuit 10.

The dialysis device 1 furthermore comprises a control device 100, which is configured to control the treatment of a patient. The control device 100 controls, for example, the functioning of the pump 9 and/or switches the clamp 12.

Furthermore, an indicating or display device 110 is provided, by which operating statuses of the dialysis device 1 may be displayed. The display device 110 in the depicted exemplary embodiment is schematically shown in the form of a monitor. However, other display devices or indicating devices are possible, such as acoustic or haptic devices.

In order to treat the blood of a prescribed dialysis patient with the dialysis device, the blood feed line 13 is connected with the circulation of the patient, for example, via a cannula. The withdrawn blood is fed via the pump 9 to the dialysis filter 5, wherein the blood is treated by means of known dialysis methods. For example, a hemodialysis, a hemofiltration, a Hemodiafiltration, or another known dialysis method may be performed in the dialysis filter 5. The treated blood is then returned to the patient via the blood return line 14, which is also connected to the circulation of the patient.

A differential pressure sensor 6 measures a differential pressure Nam between the pressure $p_1$ in the blood feed line 13, which corresponds to an arterial pressure, and the pressure $p_2$ in the blood return line 14, which corresponds to a venous pressure. The measured differential pressure Nam can be used e.g. to determine an operating status of the dialysis device 1, for example, to monitor a correct functioning of the dialysis device 1 with regard to the functioning of further pressure sensors, which are not shown in FIG. 1.

In FIG. 1, a configuration of the dialysis device 1 is schematically shown, wherein only the differential pressure sensor 6 and a monitoring unit 11, which is configured to determine an operating status based on the differential pressure $p_{diffm}$ measured by the differential pressure sensor 6, are provided.

Depending on the determined operating status based on the measured differential pressure $p_{diffm}$, the dialysis treatment is either continued in this operating status or an error notification occurs and/or the blood flow in the extracorporeal blood circuit is stopped. For this purpose, the operating status determined by the monitoring unit 11 may be communicated to the control device 100 and the control device 100 accordingly ends the treatment or blocks the beginning of a treatment. The determined operating status may, alternatively, or in addition, also be communicated to a display device 110 to be displayed thereon.

When the measured differential pressure Nam corresponds, for example, to a nominal value of a normal dialysis procedure, the dialysis procedure is continued. However, if the measured differential pressure $p_{diffm}$ deviates from this nominal value, for example, in the case, wherein the venous needle, which returns the treated blood to the patient, is dislocated or slid out or another form of needle disconnection has occurred, thereby causing a pressure drop in the blood return line 14, this is noticed by the monitoring unit 11 and an error notification to the user occurs and/or the extracorporeal blood circuit is immediately stopped to avoid a safety hazard for the patient due to a potential high blood loss.

This alarm threshold may not only be exceeded in the case of said deviation from a nominal value, but also upon a corresponding change of the differential pressure $p_{diffm}$, such that also in the case of a change of the differential pressure Nam an alarm may be triggered or the dialysis may be stopped. For example, in case of a sudden change of the differential pressure $p_{diffm}$, it may be assumed that an irregularity relating to the integrity of the connection of the extracorporeal blood circuit with the patient exists and hence a needle disconnection may have occurred.

The evaluation of the course of the differential pressure $p_{diffm}$ over time or the comparison of the measured differential pressure $p_{diffm}$ with a nominal value is provided by the monitoring unit 11, which is configured to perform the corresponding analyses. The monitoring unit 11 may e.g. be provided in the form of a hardware module and/or in the form of a software module. According to the result of the evaluation the monitoring unit 11 then sends an alarm notification and/or a command to abort or stop the dialysis treatment, when an alarm condition is achieved or exceed.

Furthermore, a control device 100 and/or a display device 110 of the dialysis device 1 may be provided. The control device 100 may be configured to interrupt or stop a dialysis treatment and/or block a future treatment based on a message from the monitoring unit 11. The display device 110 may be configured to output a notification based on the determined operating status.

The monitoring unit 11 and/or the control device 100 and/or the display device 110 may also be formed as a common unit, for example, in the form of a control device of a dialysis device with a common processor.

The monitoring unit 11 may e.g. be formed such that it may receive the signal of the differential pressure sensor 6 and may e.g. comprise one or more processors and a storage to store a program, by which the monitoring steps may be performed on the processor. The monitoring unit 11 may accordingly be realized as a computer with corresponding buses integrated in the dialysis device 1.

The control device 100 may also be provided such that only the program code for the control is different from the program code of the monitoring unit 11, wherein at least partly the same hardware is used, e.g. a common processor. The control device 100 and the monitoring unit 11 may also be present in different software modules, for example.

The control device 100 may be programmed to block or stop a treatment with the dialysis device 1, to avoid a starting of, or to stop, a blood pump. The blocking may also be provided by depicting that an action to be performed by a user is not performable. For example, an actuation field on the machine or on a display of the machine may not be activatable.

The display device 110 may be present in the form of a display screen, for example in the form of a touch screen, and/or a loud speaker to output acoustic signals and/or an optical transducer, such as a lamp.

Figure 2:
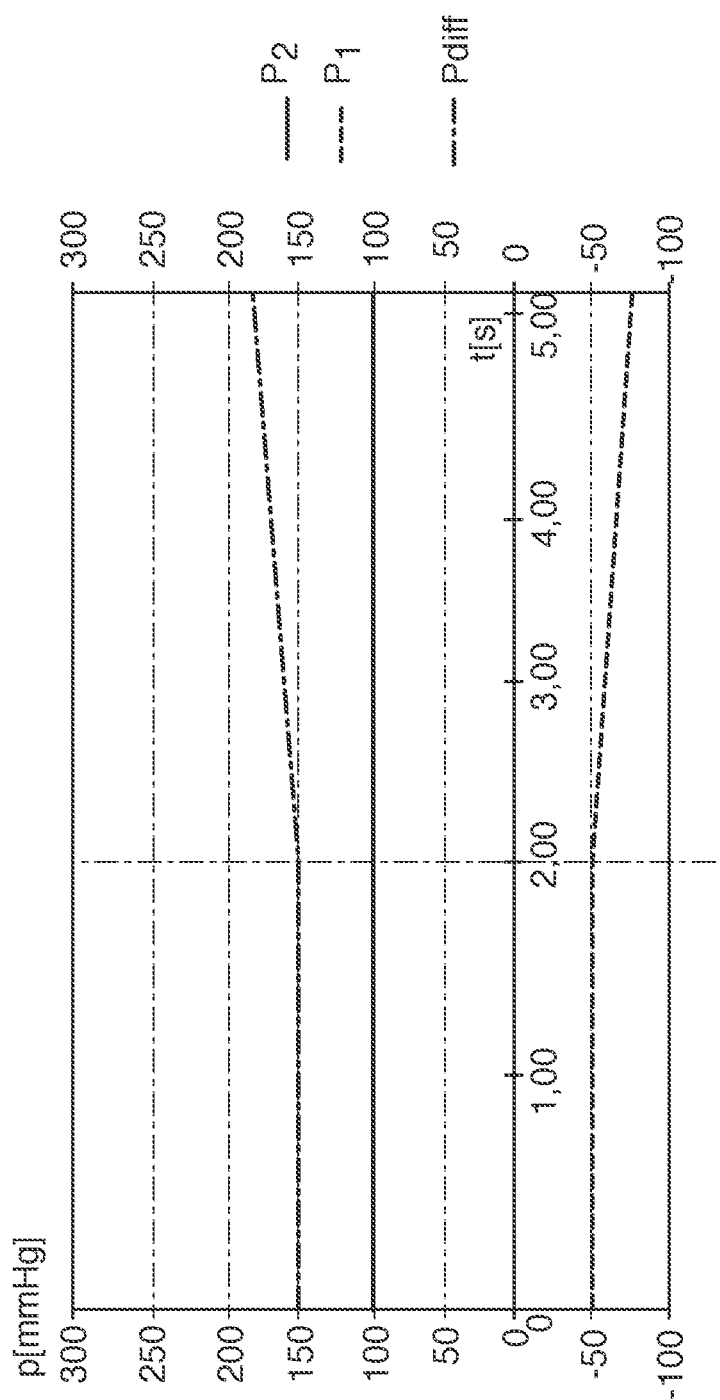
FIG. 2 is a diagram, which depicts a desirable and an undesirable operating status of the dialysis device of FIG. 1.

In FIG. 2 a diagram is shown, which depicts a desirable operating status A and an undesirable operating status B of the dialysis device 1 from FIG. 1. Here, the schematic course of the pressure p [mmHg] of the measured differential pressure $p_{diffm}$ and the schematic course of the pressure $p_1$ in the blood feed line 13 and the pressure $p_2$ in the blood return line 14 over time t [5] are plotted. The values of the pressure $p_1$ in the blood feed line 13 and the pressure $p_2$ in the blood return line 14 are only schematically depicted for illustration and are not necessarily measured directly by means of the dialysis device from FIG. 1—accordingly, no pressure measuring devices for the pressures in the blood feed line 13 and in the blood return line 14 are shown in FIG. 1.

For a simplified representation the shown pressures are depicted linearly, which may correspond e.g. to an average value of the pressures. The actual pressures may obviously vary periodically with the heart beat and the pumping movement of the pump 9. In the desired operating status A, the pressure $p_1$ in the blood feed line 13 and the pressure $p_2$ in the blood return line 14 essentially run constant at least with respect to their average value, such that also the differential pressure Nam measured by means of the differential pressure sensor 6 is essentially a constant value. In such a case, no error or failure alarm and/or command to stop the treatment is generated by the monitoring unit 11.

The undesirable operating status B schematically shows the case of an error, wherein the venous needle, which should return the purified blood to the patient, is dislocated or disconnected from the vein of the patient (VND, Venous Needle Disconnect). When a connection between the needle, i.e. the exit of the blood return line 14, and the vein of the patient no longer exists, a (marginal) pressure drop of the pressure $p_2$ in the blood return line 14 occurs. Based on said pressure drop, the differential pressure $p_{diffm}$ measured by the differential pressure sensor 6 also changes. The monitoring unit 11 detects this change of the pressure drop of the differential pressure $p_{diffm}$ and sends an error notification and/or initiates an immediate interruption of the dialysis process or the pump 9.

Figure 3:
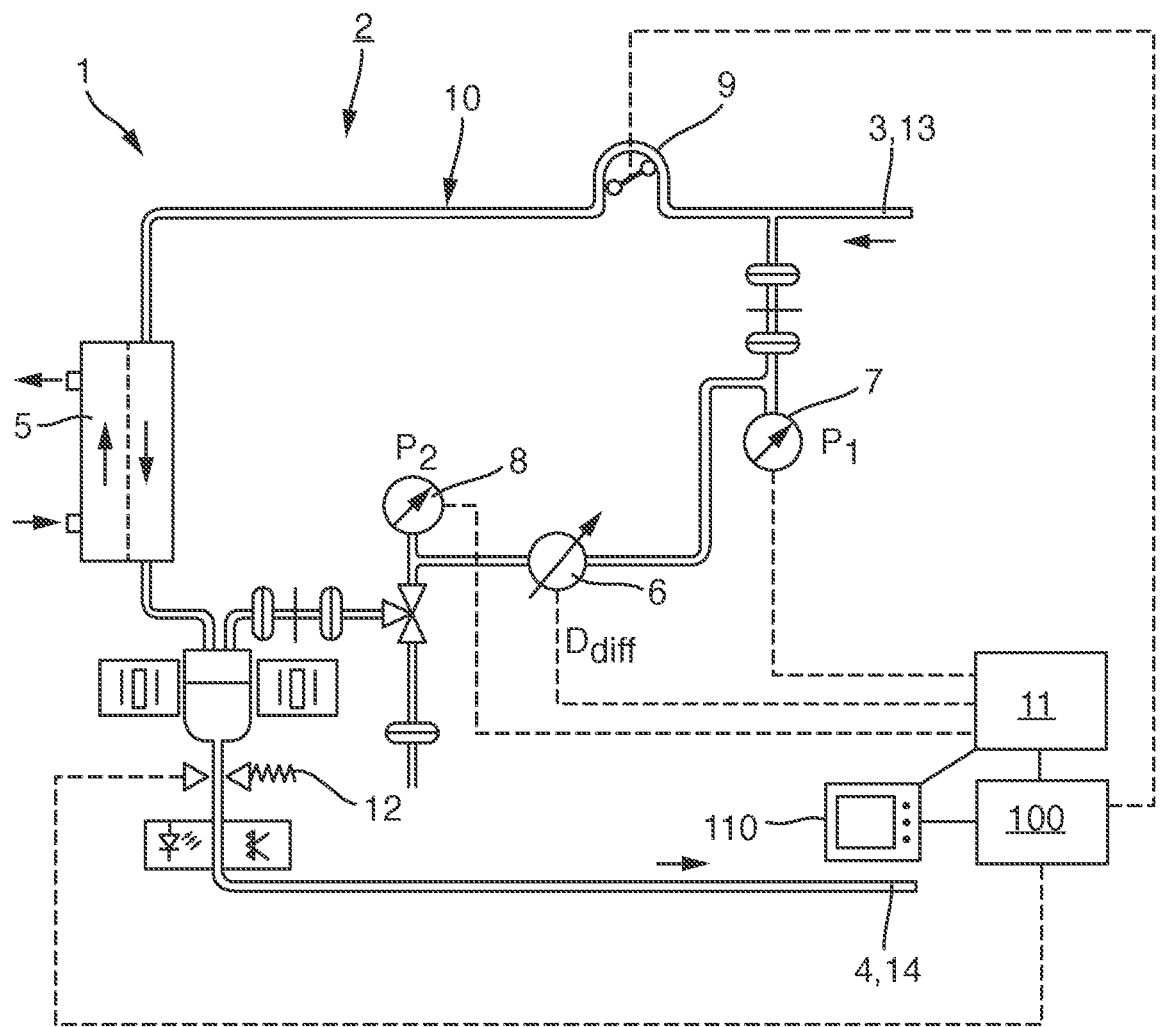
FIG. 3 shows a dialysis device with an extracorporeal blood circuit of a dialysis device having a first pressure sensor in a blood feed and a second pressure sensor in a blood return and a differential pressure sensor between the blood feed and the blood return.

In FIG. 3 a dialysis device 1 is shown with an extracorporeal blood circuit 10 having a first pressure sensor 7 arranged in a first section 3, which is arranged here at a blood feed line 13, and a second pressure sensor 8 arranged in a second section 4, which is arranged here at a blood return line 14. A differential pressure sensor 6 is depicted between the first section 3 and the second section 4. In addition, the dialysis device comprises a monitoring unit 11, which is configured to determine a correct functioning of the first and/or second pressure sensor 7, 8, and accordingly determines the operating status in this manner.

By means of the dialysis device 1 shown in FIG. 3 it is hence possible to verify or check the functioning of the first and/or second pressure sensors 7, 8.

The dialysis device 1 comprises again a pump 9 to feed the blood withdrawn from a patient and a dialysis filter 5. To treat the blood of a patient prescribed with dialysis by means of the dialysis device 1, the blood feed line 13 is connected to a vein of the patient.

The blood withdrawn from the patient is fed via the pump 9 to the dialysis filter 5, wherein the blood of the patient is purified by means of known dialysis methods, for example, a hemodialysis, a hemofiltration, a hemodiafiltration, or another dialysis method.

The purified blood is then returned to the patient via a blood return line 14, which is also connected with this vein of the patient. The differential pressure $p_{diffm}$ between the pressure $p_1$ in the blood feed line 13, i.e. the first section 3 of the liquid conducting system 2, and the pressure $p_2$ in the blood return line 14, i.e. the second section 4 of the liquid conducting system 2, is measured via the differential pressure sensor 6. In addition, the pressure $p_1$ in the first section 3 is measured by the first pressure sensor 7 and the pressure $p_2$ in the second section 4 is measured by the second pressure sensor 8.

If the measured differential pressure Nam is considered individually, an assessment may be made regarding the operating status of the dialysis device 1 and the dialysis method may be accordingly continued or interrupted, as already described in view of FIG. 1.

In order to carry out a monitoring of the first and/or second pressure sensor 7, 8, a differential pressure $p_{diffb}$ is calculated in the monitoring unit 11 from the measured pressure $p_1$ in the first section 3 and the measured pressure $p_2$ in the second section 4. Then, the differential pressure $p_{diffm}$ as measured by the differential pressure sensor 6 and the calculated differential pressure $p_{diffb}$ are compared with each other, for example, subtracted from each other. From the comparison between the measured differential pressure Nam and the calculated differential pressure $p_{diffb}$, a resulting pressure pies is obtained.

In the case, wherein both pressure sensors 7, 8 are functioning correctly, i.e. wherein the pressure sensor 7 correctly measures the pressure $p_1$ in the first section 3 and the pressure section 8 correctly measures the pressure $p_2$ in the second section 4, the measured differential pressure and the calculated differential pressure correspond to each other, i.e. the resulting pressure pies is zero or at least constant over time.

In the case wherein both pressure sensors 7, 8 are not functioning correctly, i.e. wherein the pressure sensor 7 does not correctly measure the pressure $p_1$ in the first section 3 and the pressure section 8 does not correctly measure the pressure $p_2$ in the second section 4, the measured differential pressure $p_{diffm}$ and the calculated differential pressure $p_{diffb}$ do not correspond to each other, i.e. the resulting pressure $p_{res}$ does not equal zero or changes over time. The evaluation of the resulting pressure $p_{res}$, i.e. the calculation of the resulting pressure $p_{res}$ from the measured differential pressure $p_{diffm}$ and the calculated differential pressure $p_{diffb}$ and the comparison to a nominal value (for example zero) is performed by the monitoring unit 11. When a deviation of the resulting pressure $p_{res}$ from the nominal value is detected, an error notification occurs and/or the extracorporeal blood circuit 10 is stopped.

Figure 4:
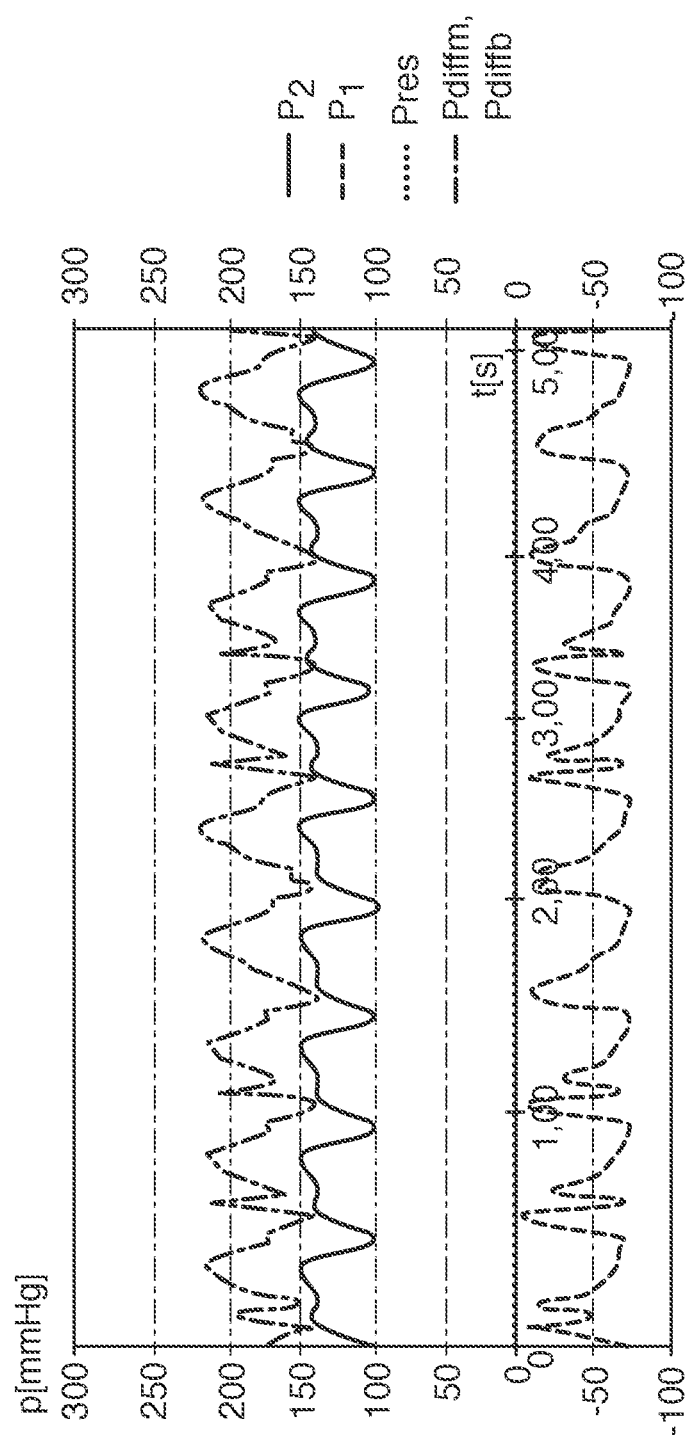
FIG. 4 is a diagram, which indicates an exemplary pressure course of the dialysis device of FIG. 3 with correctly measuring pressure sensors.

An exemplary pressure course is schematically shown in FIG. 4 for the case wherein both pressure sensors 7, 8 are measuring correctly. The diagram in FIG. 4 shows the measured pressure $p_1$, $p_2$, $p_{diffm}$, and the calculated pressures $p_{diffb}$ and $p_{res}$. The pressure course p [mmHg] over time t [s] is plotted for each pressure. As evident from the diagram, do the calculated differential pressure $p_{diffb}$ and the measured differential pressure Nam correspond to each other, i.e. the difference between the calculated differential pressure $p_{diffb}$ and the measured differential pressure $p_{diffm}$ is zero. In this case, no error notification is provided by the monitoring unit 11 and the dialysis method is continued.

In the case, wherein the pressure sensors 6, 7, 8 having a level of tolerance are used, a difference will exist between the measured and hence tolerance containing differential pressure $p_{diffm}$ and the calculated differential pressure $p_{diffb}$, which also comprises a tolerance, as it is calculated from two tolerance containing measurement values $p_1$, $p_2$, such that the resulting pressure does not equal zero, but is essentially constant over time. The analysis by the monitoring unit 11 may take this into account and may hence still consider a deviation from the resulting pressure from the zero-line in the range of a predefined tolerance to not constitute an error.

Figure 5:
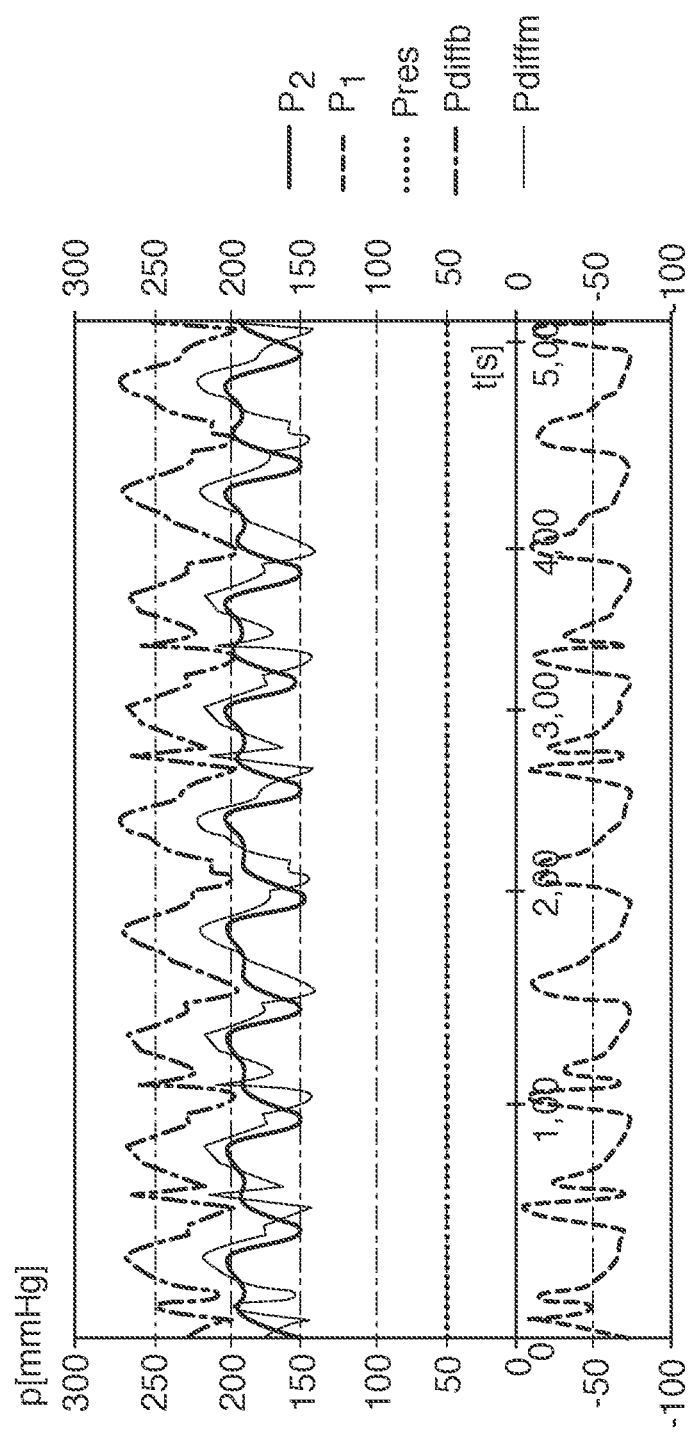
FIG. 5 is a diagram, which indicates an exemplary pressure course of the dialysis device of FIG. 3, wherein a second pressure sensor incorrectly measures in the blood return.

In FIG. 5 a schematic diagram is depicted, which shows an exemplary pressure course for the case, wherein the second pressure sensor 8, which should measure the pressure $p_2$ in the blood return, does not measure correctly. The diagram in FIG. 5 shows the measured pressures $p_1$, $p_2$, $p_{diffm}$ and the calculated pressures $p_{diffb}$ and $p_{res}$. The pressure course p [mmHg] is plotted over time t [5].

As evident from the diagram, the calculated differential pressure $p_{diffb}$ and the measured differential pressure $p_{diffm}$ do not correspond to each other, i.e. the difference between the calculated differential pressure $p_{diffb}$ and the measured differential pressure $p_{diffm}$ does not equal zero and the deviation exceeds a predefined tolerance. The monitoring unit 11 detects said deviation of the measured differential pressure $p_{diffm}$ from a nominal value and sends an error notification or stops the extracorporeal blood circuit 10.

Figure 6:
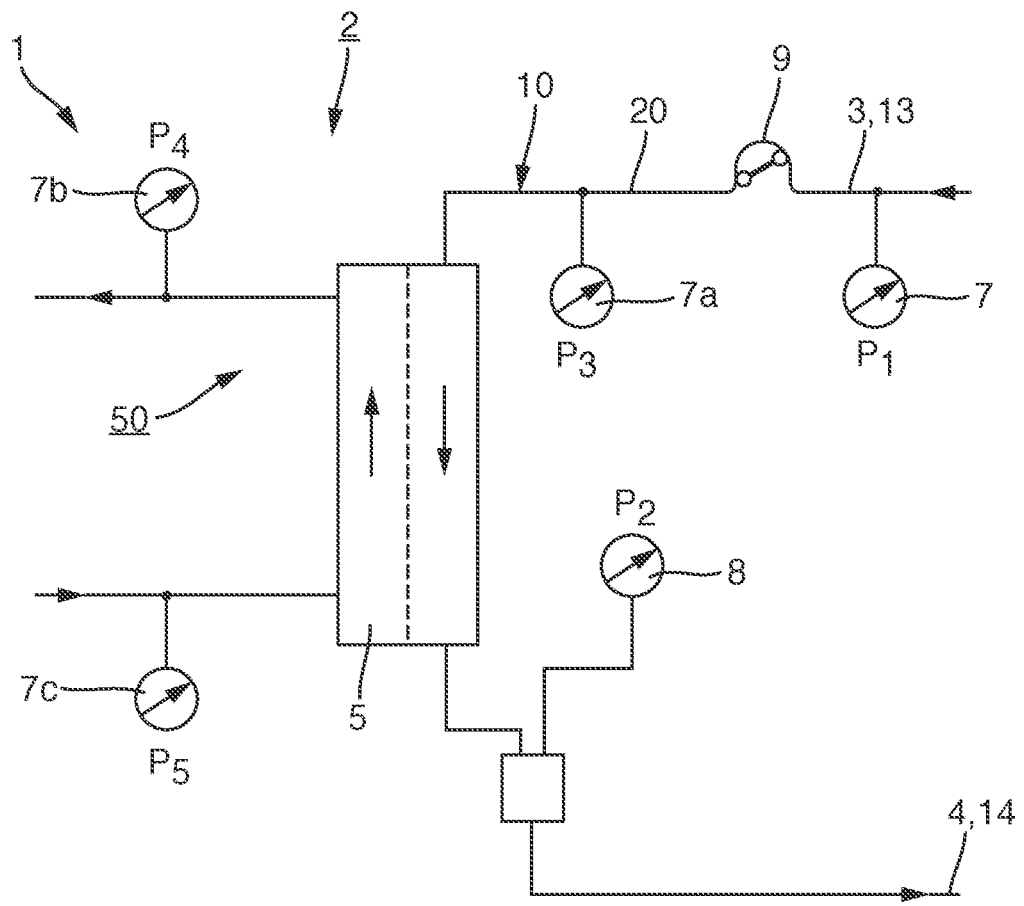
FIG. 6 shows a dialysis device with an extracorporeal blood circuit of a dialysis device, wherein various arrangement possibilities of pressure sensors, which may measure the pressure in various sections, are illustrated.
Figure 7:
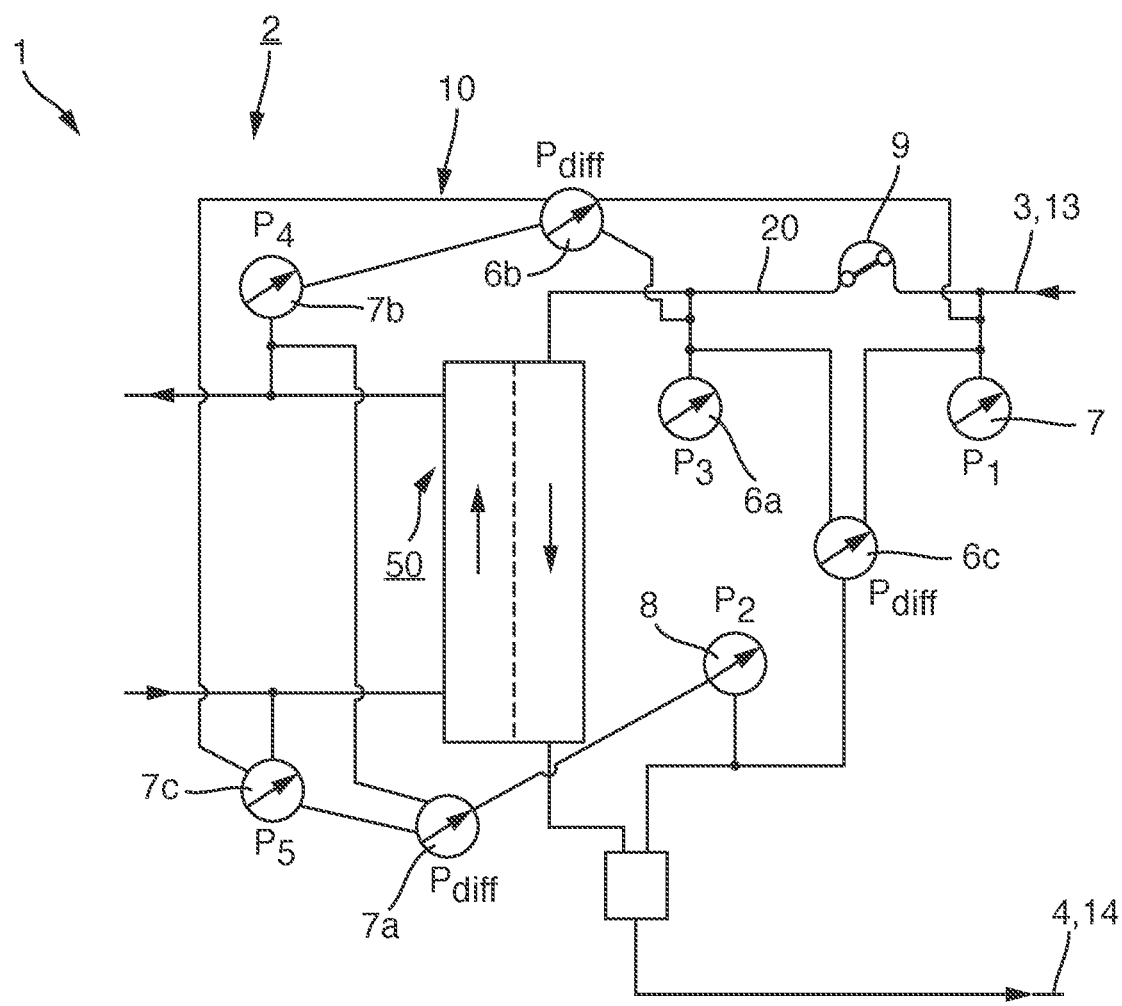
FIG. 7 shows a dialysis device with an extracorporeal blood circuit of a dialysis device, wherein further arrangement possibilities of the differential pressure sensor are illustrated.

In each of the FIGS. 6 and 7 a dialysis device 1 is shown with an extracorporeal blood circuit 10 having a first pressure sensor 7 arranged in a first section 3, which corresponds to the blood feed line 13, and a second pressure sensor 8 arranged in a second section 4, which corresponds to the blood return line 14. As described in the above, differential pressure sensors may be arranged between different or various sections of the liquid conducting system 2 and the functioning of the pressure sensors arranged at said sections may accordingly be monitored by the respective differential pressure sensor.

Accordingly, various different sections of the liquid conducting system 2 as well as pressure sensors measuring the pressure in said sections are exemplary shown in FIG. 6.

Hence, pressure sensors are shown in the form of a pressure sensor 7 for determining a pressure $p_1$ between an arterial end of the arterial feed 13 and the blood pump 9, a pressure sensor 8 for determining the pressure $p_2$ between a venous end of the venous blood return 13 and the dialyzer or dialysis filter 5, a pressure sensor 7a for determining a pressure $p_3$ in a section 20 of the liquid conducting system 2 between the blood pump 9 and the dialyzer or dialysis filter 5, a pressure sensor 7b for determining a pressure $p_4$ in a dialysate line downstream of the dialyzer 5, and/or a pressure sensor 7c for determining a pressure $p_5$ in the dialysate line upstream of the dialyzer 5. The dialyzer 5 forms a dialysis liquid circuit 50 with its feed lines and return lines.

In FIG. 7 various sections of the liquid conducting system 2 and corresponding differential pressure sensors for measuring the differential pressure between said sections are shown in FIG. 7.

In this Figure, various arrangement possibilities of differential pressure sensors 6a to 6c are illustrated. The pressure sensors 6a to 6c may be positioned in sections of ranges with various pressure regimes. The dialysis device 1, which is shown in FIGS. 6 and 7, comprises according to the pressure sensors 7a to 7c and the differential pressure sensors 6a to 6c respective individual or combined monitoring units, which are, however, not depicted to provide a better overview.

In the sections between which a differential pressure sensor 6a to 6c is arranged, an element may be positioned, which may influence, due to its resistance, the pressure transmission from a first section, e.g. a blood feed line 13, to a second section 4, e.g. a blood return line 14. This element may be e.g. a pump, in particular a peristaltic pump, hollow fibers of a dialysis membrane, a dialysis membrane, a flow reducer, a valve, a chamber that is partly filled during operation, or a similar element. Said element may also be a pressure generating element, for example, a pump, wherein the pressure fluctuations before and after said element are in phase to each other.

If said pressure influencing elements are passive elements and if the pressures in both of the sections 3, 4, are generated by completely different pressure generators, e.g. by two pumps that operate independently from each other, it may be required to average the signal over a predefined time in order to average these independent fluctuations of the pressure signals to a stable value. This may e.g. be the case, when the first section is positioned in the extracorporeal blood circuit 10 and the second section is positioned on the side of the dialysis liquid circuit 50.

The dialysis device 1 may also comprise a differential pressure sensor 6a to 6c, which is connected to more than two sections 3, 4. Furthermore, a control (not shown) may be provided, which is configured to respectively connect exactly two sections 3, 4 via the differential pressure sensor 6a to 6c and to perform one of the described monitoring methods for these sections 3, 4 and/or the pressure sensors 7a to 7c connected with said sections.

In the storage unit (memory) of the dialysis device 1 it may be stored how long or for how many measurement values the averaging must be applied, dependent on the respectively connected sections or pressure sensors.

A further parameter, which is stored in the storage unit, for the duration or the number of the measurement values for the averaging, may also be the velocity, with which the pumps of the dialysis device transport the liquid through the respective sections 3, 4. For this purpose, e.g. a chart or table or an equation may be stored in the storage unit. In the case, wherein the pressures of the individual sections 3, 4 are each measured by independent pressure sensors, the pressure courses may be averaged by means of a program being run by a processor in the dialysis device until the fluctuations of the pressure courses have dropped below a predefined threshold stored in the storage unit.

Figure 8:
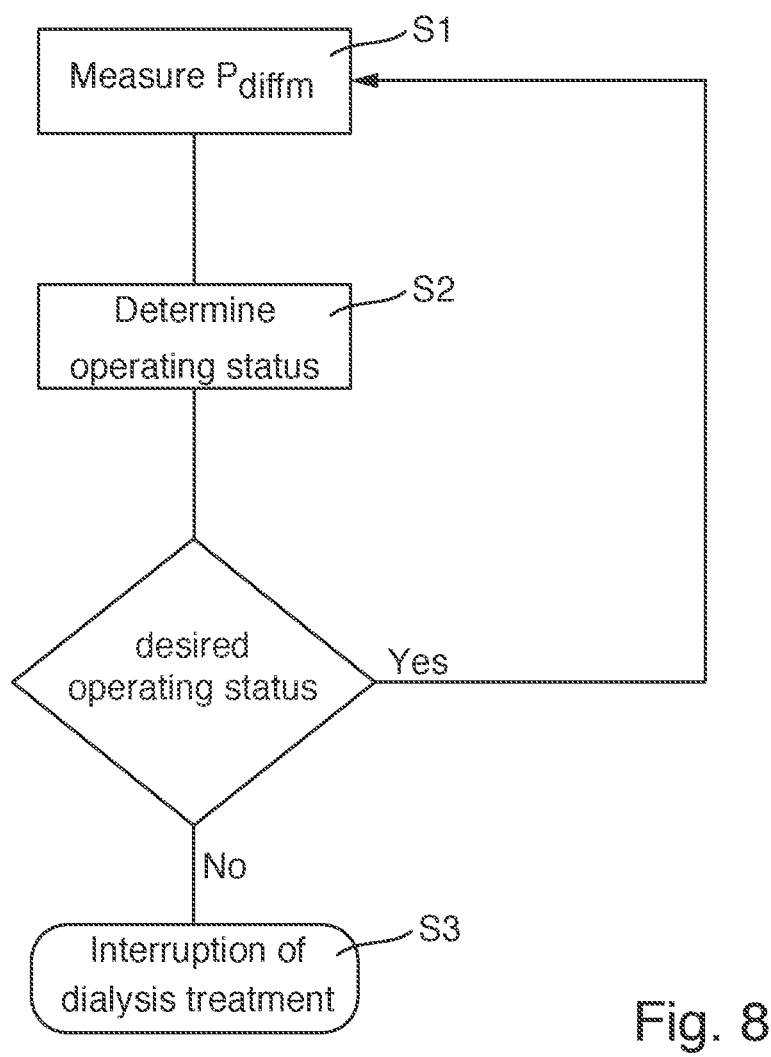
FIG. 8 is a schematic representation of the method for monitoring an operating status of a dialysis device based on a measured differential pressure.

In FIG. 8 a method for monitoring an operating status of a dialysis device is shown in a schematic depiction. The method is preferably performed with a dialysis device 1 as described in the above, which comprises a liquid conducting system 2 with a first section 3 and a second section 4.

In a first step S1 of the depicted method, a differential pressure $p_{diffm}$ is measured between a first pressure $p_1$ in the section 3 and a second pressure $p_2$ in the second section by means of a differential pressure sensor 6.

In a second step S2 an operating status is determined based on the measured differential pressure $p_{diffm}$.

When an undesirable operating status is determined in step S2, e.g. in the case, wherein the venous needle, by which the purified blood is returned to the patient, is accidentally disconnected from the venous patient access of the patient (VND, Venous Needle Disconnect), the treatment is either immediately interrupted to avoid a safety hazard for the patient and/or a notification is outputted, e.g. via a display device 110, in step S4.

When the determining of the operating status in step S2 results in the presence of a desirable operating status, e.g. in the case, wherein the differential pressure is essentially constant and the dialysis may hence be safely and effectively performed, the treatment is continued.

Figure 9:
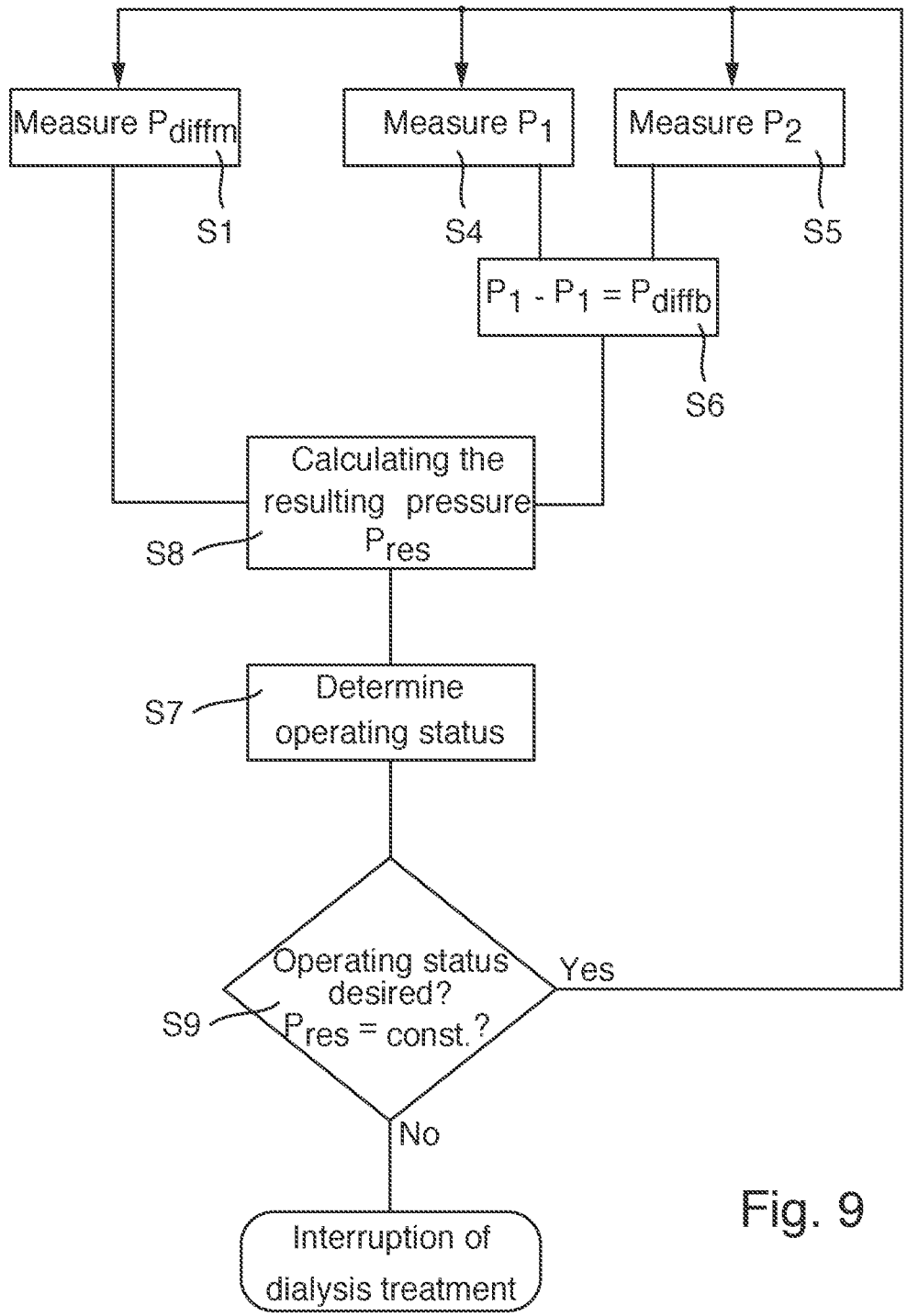
FIG. 9 is a schematic representation of the method for monitoring an operating status of a dialysis device based on a calculated and a measured differential pressure.

In FIG. 9 a schematic depiction of the method for monitoring an operating status of a dialysis device 1 based on a calculated differential pressure $p_{diffb}$ and a measured differential pressure Nam is shown.

In a step S4 a first pressure $p_1$ is measured in a first section 3. In a step S5, a second pressure $p_2$ is measured in a second section 4. By means of the measured first pressure $p_1$ and the measured second pressure $p_2$ a differential pressure $p_{diffb}$ is calculated in a step S6.

In a step S1, a differential pressure $p_{diffm}$ between the first pressure $p_1$ in the section 3 and the second pressure $p_2$ in the second section 4 is measured by means of the differential pressure sensor 6, either in parallel, thereafter, or also beforehand.

By means of the calculated differential pressure $p_{diffb}$ and the measured differential pressure $p_{diffm}$ a resulting pressure $p_{res}$ is calculated in a step S8.

Based on the calculated resulting pressure $p_{res}$, the operating status of the dialysis device 1 is determined in a step S7 and an analysis is performed in a step S9. When the analysis provides that an undesirable operating status exists, the dialysis treatment is interrupted.

Where applicable, all of the individual features that are depicted in the exemplary embodiments may be combined and/or replaced without leaving the scope of the present disclosure.

LIST OF REFERENCE NUMERALS

1 Dialysis device
2 Liquid conducting system
3 First section
4 Second section
5 Dialysis filter
6 Differential pressure sensor
6a-6c Differential pressure sensor
7 First pressure sensor
7a-7c Pressure sensor
8 Second pressure sensor
9 Pump
10 Extracorporeal blood circuit
11 Monitoring unit for determining an operating status
12 Clamp
13 Blood feed
14 Blood return
100 Control device
110 Display device
$p_1$ First pressure
$p_2$ Second pressure
$p_{art}$ Arterial pressure $p_{ven}$ Venous pressure
$p_{diffm}$ Measured differential pressure
$p_{diffb}$ Calculated differential pressure
$p_{res}$ Resulting differential pressure
A Desired operating status
B Undesired operating status
S1 Measuring differential pressure $p_{diffm}$
S2 Determining the operating status
S3 Interrupting a dialysis treatment
S4 Measuring of the pressure $p_1$
S5 Measuring of the pressure $p_2$
S6 Calculating the differential pressure $p_{diffb}$
S7 Determining the operating status
S8 Calculating a resulting pressure pies
S9 Analysis

The invention claimed is:

1. A dialysis device for performing a dialysis treatment, the dialysis device comprising:
    a liquid conducting system comprising a first section and a second section;
    a first pressure sensor arranged for measuring a first pressure in the first section;
    a second pressure sensor arranged for measuring a second pressure in the second section;
    a differential pressure sensor arranged for measuring a differential pressure $p_{diffm}$ between the first section of the liquid conducting system and the second section of the liquid conducting system;
    a monitoring unit configured to (i) calculate a differential pressure $p_{diffb}$ between the first pressure measured by the first pressure sensor and the second pressure measured by the second pressure sensor and (ii) determine an operating status based on the measured differential pressure $p_{diffm}$, wherein the monitoring device is further configured to:
        determine the operating status by comparing the calculated differential pressure $p_{diffb}$ and the measured differential pressure $p_{diffm}$, or
        determine a difference between the calculated differential pressure $p_{diffb}$ and the measured differential pressure $p_{diffm}$ and to compare the determined difference with a nominal value to determine the operating status; and
    a control device configured to interrupt and/or block the dialysis treatment according to the determined operating status, and/or a display device configured to output a notification based on the determined operating status.

2. The dialysis device according to claim 1, wherein the determined operating status indicates an incorrect functioning of the first pressure sensor and/or the second pressure sensor.

3. The dialysis device according to claim 1, wherein the first section and the second section of the liquid conducting system comprise portions of an extracorporeal blood circuit that includes a dialysis filter, wherein the first section corresponds to a blood feed line and the second section corresponds to a blood return line.

4. The dialysis device according to claim 3, wherein the monitoring unit is configured to detect a needle disconnection as an operating status based on the measured differential pressure $p_{diffm}$ and/or a change of the measured differential pressure $p_{diffm}$.

5. The dialysis device according to claim 1, wherein the monitoring device is configured to calculate a resulting pressure $p_{res}$ from the difference between the calculated differential pressure $p_{diffb}$ and the measured differential pressure $p_{diffm}$, and analyze behavior of the resulting pressure $p_{res}$.

6. The dialysis device according to claim 5, wherein analyzing the behavior comprises a comparison with a nominal value and/or an analysis of the change over time.

7. The dialysis device according to claim 6, wherein an error volume is accumulated from the resulting pressure $p_{res}$ when the resulting pressure $p_{res}$ deviates from the nominal value, and the control device is configured to provide the notification when a predefined maximum error volume is exceeded.

8. The dialysis device according to claim 7, wherein the control device is configured to provide the notification when a persisting deviation of the resulting pressure $p_{res}$ from the nominal value is provided and a minimum trigger level is reached.

9. A method for monitoring an operating status of a dialysis device comprising a liquid conducting system with a first section and a second section, the method comprising:
    measuring a differential pressure $p_{diffm}$ between a first pressure ($p_1$) in the first section and a second pressure ($p_2$) in the second section using a differential pressure sensor,
    calculating a differential pressure $p_{diffb}$ between the first pressure in the first section and the second pressure in the second section,
    determining an operating status by comparing the calculated differential pressure $p_{diffb}$ measured differential pressure $p_{diffm}$, and
    interrupting a dialysis treatment and/or blocking a dialysis treatment and/or outputting a notification based on the determined operating status.

10. A method for monitoring an operating status of a dialysis device comprising a liquid conducting system with a first section and a second section, the method comprising:
    measuring a differential pressure $p_{diffm}$ between a first pressure ($p_1$) in the first section and a second pressure ($p_2$) in the second section using a differential pressure sensor,
    calculating a differential pressure $p_{diffb}$ between the first pressure in the first section and the second pressure in the second section,
    determining a difference between the calculated differential pressure $p_{diffb}$ and the measured differential pressure $p_{diffm}$ and comparing the determined difference with a nominal value to determine an operating status, and
    interrupting a dialysis treatment and/or blocking a dialysis treatment and/or outputting a notification based on the determined operating status.

* * * * *